(12) United States Patent
Claiborne et al.

(10) Patent No.: US 6,319,944 B1
(45) Date of Patent: Nov. 20, 2001

(54) ARYL AMIDINES, COMPOSITIONS CONTAINING SUCH COMPOUNDS AND METHODS OF USE

(75) Inventors: Christopher F. Claiborne, Lansdale; Nigel J. Liverton, Harleysville; Brian Libby, North Wales, all of PA (US); Neil R. Curtis; Janusz Kulagowski, both of Harlow (GB)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/564,835

(22) Filed: May 4, 2000

Related U.S. Application Data

(60) Provisional application No. 60/133,347, filed on May 10, 1999.

(51) Int. Cl.[7] .................. A61K 31/335; A61K 31/41; A61K 31/405; A61K 31/155
(52) U.S. Cl. ............... 514/452; 514/361; 514/415; 514/466; 514/631; 514/637; 514/469; 549/366; 549/440; 548/125; 548/127; 564/225; 564/244
(58) Field of Search ................. 564/225, 244; 549/440, 366; 548/127, 125, 469; 514/466, 452, 631, 361, 637, 415

(56) References Cited

U.S. PATENT DOCUMENTS 5,672,620 9/1997 Scherz et al. .

FOREIGN PATENT DOCUMENTS 2081555 10/1971 (FR) .

OTHER PUBLICATIONS

D.J. Knox et al., Anaesthesia and Intensive Care, 23: 620–622 (1995).
A. Wenzel et al., Neuro Report, 7: 45–48 (1995).
I.J. Mitchell et al., Behavioural Pharmacology, 6: 492–507(1995).
L. Bezin et al., Mol. Brain Res., 50: 23–32(1997).
P.J. Whiting et al., "Molecular biology of N–methyl–D–aspartate (NMDA)–type glutamate receptors," Amino Acid Neurotransmission, A.J.Turner and F. Anne Stephenson, Ed., Portland Press, London, 1998.
K. Taniguchi et al., Brit. J. Pharmacology, 122: 809–812(1997).
T. Sakurada et al., Pharmacology Biochem. and Behavior, 59: 339–345 (1998).
J.E. Nash et al., Exp. Neurology, 155: 42–48(1999).
M.B. Max et al., Clin. Neuropharmacology, 18: 360–368(1995).
T. Ishii et al., J. Biol. Chem., 268: 2836–2843 (1993).
O. Hornykiewicz, Pharmacological Rev., 18: 925–964(1966).
S. Grimwood et al., J. Neurochem., 66: 2239–2247(1996).
S. Grimwood et al., J. Neurochem., 66: 2589–2595(1996).
P.K. Eide et al., Pain, 61: 221–228(1995).
S. Boyce et al., Neuropharmacology, 38: 611–623 (1999).
S. Boyce et al., Neuropharmacology, 33: 1609–1611 (1994).
J.D. Kristensen et al., Pain, 51:249–253(1992).
Derwent Database Accession No. 1968: 67609 HCAPLUS, A Popova et al., Dokl.Bolg.Akad.Nauk., 20: 1365–1368(1967).
Derwent Database Abstract Printout AN: 1972–11903T.
Robev, S 'Production of pyrimidine derivatives by reacting aromatic N–monoaryl substituted amidines with ylidenmalononitriles' CA 87:167970, 1977.*
Gruppo Lepetit 'Triazoloisoindole derivatives' CA 83:206286, 1975.*
Robev, S 'Synthesis of some halogenated aromatic N–aryl–substituted amidines' CA 70:67829, 1969.*

\* cited by examiner

*Primary Examiner*—Amelia Owens
(74) *Attorney, Agent, or Firm*—Shu M. Lee; David L. Rose

(57) ABSTRACT

Compounds represented by formula I:

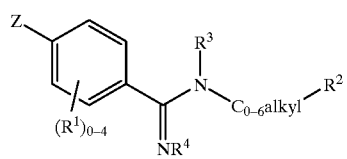

or a pharmaceutically acceptable salt or hydrate thereof, are disclosed.

Pharmaceutical compositions and methods of treatment are also included.

22 Claims, No Drawings

ARYL AMIDINES, COMPOSITIONS CONTAINING SUCH COMPOUNDS AND METHODS OF USE

This appln claims benefit of Prov. No. 60/133,347 filed May 10, 1999.

BACKGROUND OF THE INVENTION

The invention relates to novel aryl amidines, compositions containing such compounds and methods of treating neurological and neurodegenerative diseases. In particluar, this invention relates to amidines that are useful as NMDA NR2B antagonists. The compounds of the instant invention are thus useful for relieving, treating or preventing neurological and neurodegenerative diseases, including pain, (and in particular neuropathic pain), epilepsy, stroke, anxiety, cerebral ischemia, muscular spasms, Alzheimer's Disease, Huntington's Disease and Parkinson's Disease.

Evidence for the analgesic effects of NMDA receptor antagonists in man is strong. Ion channel antagonists such as ketamine and dextromethorphan produce hallucinations, sedation, and ataxia at doses only marginally higher than the analgesic dose. The NR2B receptor is found presynaptically on most small sensory fibres entering the spinal dorsal horn as well as postsynaptically unlike other NMDA receptors which are exclusively postsynaptic. This restricted distribution lowers the probability of side effects and makes the target highly attractive for the treatment of neuropathic and other pain conditions.

Glutamate plays a key role in processes related to chronic pain and pain-associated neurotoxicity, largely acting through N-methyl-D-aspartate (NMDA) receptors. Much evidence points to the involvement of NMDA receptors in the development and maintenance of neuropathic pain. NMDA receptor antagonists, for example ketamine, dextromethorphan and CPP (3-(2-carboxypiperazin-4-yl)-propyl-1-phosphonic acid) have been reported to produce symptomatic relief in a number of neuropathies including postherpetic neuralgia, central pain caused by spinal cord injury and phantom limb pain (Kristensen et al., 1992; Eide et al., 1995; Knox et al., 1995; Max et al., 1995). However, at analgesic doses, psychotomimetic effects that include dizziness, headache, hallucinations, dysphoria and disturbances of cognitive and motor function prohibit their widespread use. To exploit NMDA receptor antagonists as possible treatment modalities for neuropathic pain, it is necessary to develop new agents with a reduced side-effect profile.

Native NMDA receptors are heterodimers composed of an NMDA R1 (NR1) subunit and at least one NMDA R2 (NR2) subunit. Receptor cloning strategies have identified multiple NMDA receptor subunits in the CNS including the NR1 subfamily (with eight isoforms derived from alternative splicing of a single gene) and four NR2 subunits (A, B, C, and D) each encoded by a single gene (for review, see Whiting & Priestly, 1996). Functional receptors have different physiological and pharmacological properties and are differentially distributed in the mammalian CNS, demonstrating the functional heterogeneity of NMDA receptors (Ishii et al., 1993; Wenzel et al., 1995; Laurie et al., 1997).

NR1 is found throughout the brain whereas NR2 subunits show a differential distribution. In particular whereas NR2C is heavily expressed and NR2A is moderately expressed in the cerebellum, there is negligible expression of NR2B in this structure. Immunocytochemical studies have demonstrated a restricted distribution of the NR2B subunit, with moderate labeling of fibres in laminas I and II of the dorsal horn suggesting a presynaptic location on primary afferent fibres and possible involvement in pain transmission (Boyce et al., 1999). The patterns of staining observed in the spinal cord, together with the data showing negligible expression of NR2B in the cerebellum, suggest that NR2B antagonists may possess antinociceptive effects, but with a reduced side effect profile than non-competitive NMDA antagonists or glycine site antagonists.

The NR2B selective antagonist CP-101,606 has been reported to possess antinociceptive activity in animal assays of inflammatory hyperalgesia (Taniguchi et al., 1997; Sakurada et al, 1998). In an animal assay of inflammatory hyperalgesia (carrageenan-induced mechanical hyperalgesia) NR2B antagonists CP-101,606 and Ro 25-6981 possess antinociceptive activity with a significant separation between analgesic doses and those which induced motor impairment (Boyce et al., 1999). NR2B antagonists are active in a wide range of animal nociceptive assays, suggesting a clinical utility for other painful conditions in addition to those caused by nerve damage. Moreover these compounds may have a reduced propensity to elicit the ataxic effects of ketamine and other NMDA ion channel antagonists.

There is a wealth of in vitro and animal model data which suggests that changes in the glutamatergic system (receptors, uptake, release) increase neuronal sensitivity to previous physiological stimuli and thereby trigger secondary neuronal damage. The primary pathology underlying the generation of symptoms in Parkinson's disease is degeneration of dopaminergic neurons of the nigrostriatal pathway (Hornykiewcz, 1966). Subsequent to loss of striatal dopamine, a series of changes in activity of the basal ganglia circuitry arise, including increased activity in striatal outputs to the lateral segment of the globus pallidus. Overactivity of the striatolateral pallidal pathway is thought to be responsible for the generation of parkinsonian symptoms. It has been demonstrated that selective blockade of NR2B-containing NMDA receptors with the polyamine antagonists ifenprodil and eliprodil cause a significant increase in locomoter activity in a rodent model (Nash et al., 1999) and ifenprodil has demonstrated activity in a primate model of Parkinson's disease (Mitchell et al., 1995).

Based upon the foregoing, one object of the present invention is to provide NR2B active compounds with a reduced side effect profile compared to conventional agents.

Another object is to expoit the NR2B pathway with new treatment modalities.

Another object is to provide compounds that are useful in controlling neuropathic pain. These and other objectives will be obvious to those of ordinary skill from the teachings contained herein.

SUMMARY OF THE INVENTION

A compound represented by formula I:

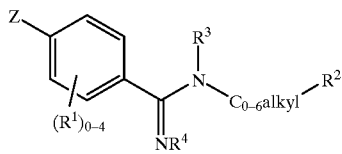

I or a pharmaceutically acceptable salt or hydrate thereof, wherein:

each $R^1$ independently represents a member selected from the group consisting of: halo, $C_{1-7}$ alkyl, halo$C_{1-7}$ alkyl, OH, O$C_{1-7}$ alkyl, and halo$C_{1-7}$ alkoxy, and Z represents a member selected from the group consisting of: H, halo, $C_{1-7}$ alkyl, halo$C_{1-7}$ alkyl, OH, halo$C_{1-7}$ alkoxy and aryl, or one $R^1$ group and Z or two $R^1$ groups taken in combination represent a fused aryl, heteroaryl or heterocyclyl group, said fused group being optionally substituted with 1–4 groups selected from OH, halo, $C_{1-7}$ alkyl, sulfonyl, cyano, O$C_{1-7}$ alkyl, halo$C_{1-7}$ alkyl and halo$C_{1-7}$ alkoxy and the remaining $R^1$ groups are as originally defined;

$R^3$ and $R^4$ independently represent H, $C_{1-7}$ alkyl, $C_{2-4}$ alkenyl, $C_{2-4}$ alkynyl, aryl or heterocyclyl; and $R^2$ represents H, aryl or heteroaryl, said aryl or heteroaryl being optionally substituted with 1–3 groups selected from: halo, OH, $C_{1-7}$ alkyl, O$C_{1-7}$ alkyl, halo$C_{1-7}$ alkyl and halo$C_{1-7}$ alkoxy.

Pharmaceutical compositions and methods of treatment are also included.

DETAILED DESCRIPTION

The present invention includes compounds represented by formula I:

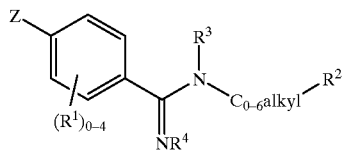

I or a pharmaceutically acceptable salt or hydrate thereof, wherein:

each $R^1$ independently represents a member selected from the group consisting of: halo, $C_{1-7}$ alkyl, halo$C_{1-7}$ alkyl, OH, O$C_{1-7}$ alkyl, and halo$C_{1-7}$ alkoxy, and Z represents a member selected from the group consisting of: H, halo, $C_{1-7}$ alkyl, halo$C_{1-7}$ alkyl, OH, halo$C_{1-7}$ alkoxy and aryl, or one $R^1$ group and Z or two $R^1$ groups taken in combination represent a fused aryl, heteroaryl or heterocyclyl group, said fused group being optionally substituted with 1–4 groups selected from OH, halo, $C_{1-7}$ alkyl, sulfonyl, cyano, O$C_{1-7}$ alkyl, halo$C_{1-7}$ alkyl and halo$C_{1-7}$ alkoxy and the remaining $R^1$ groups are as originally defined;

$R^3$ and $R^4$ independently represent H, $C_{1-7}$ alkyl, $C_{2-4}$ alkenyl, $C_{2-4}$ alkynyl, aryl or heterocyclyl; and $R^2$ represents H, aryl or heteroaryl, said aryl or heteroaryl being optionally substituted with 1–3 groups selected from: halo, OH, $C_{1-7}$ alkyl, O$C_{1-7}$ alkyl, halo$C_{1-7}$ alkyl and halo$C_{1-7}$ alkoxy.

The invention is described in detail using the following definitions unless otherwise indicated.

Halo includes F, Cl, Br and I. Halo$C_{1-7}$ alkyl refers to an alkyl group having 1–9 halo groups attached, up to complete substitution with halo groups, e.g., perhaloalkyl. The preferred halo group herein is F. Examples include —$CH_2F$, —$CHF_2$, —$CF_3$, —$CH_2CH_2F$, —$CHFCH_2F$, —$CF_2CH_2F$, —$CH_2CF_3$, —$CF_2CHF_2$ and —$CF_2CF_3$.

Alkyl groups include straight or branched alkyl groups having 1–7 carbon atoms, and cyclic alkyl groups having from 3–7 carbon atoms. Cycloalkyl groups with alkyl substituent groups attached are also included. Examples of $C_{1-7}$ alkyl groups include methyl, ethyl, propyl, 2-propyl, n-, s- and t-butyl, pentyl, hexyl, cyclopropyl, cyclobutyl, cyclopentyl and cyclohexyl. Examples of $C_{1-6}$ alkoxy groups include methoxy, ethoxy, propoxy, isopropoxy, cyclopropyloxy, cyclohexyloxy and the like.

Alkoxy means alkoxy groups of one to ten carbon atoms of a straight, branched or cyclic configuration. Examples of alkoxy groups include methoxy, ethoxy, propoxy, isopropoxy and the like.

"Aryl" refers to mono- or bicyclic aromatic groups containing 6–10 carbon atoms, and is selected from phenyl and naphthyl.

Heteroaryl refers to mono-, bi- or tricyclic aromatic groups containing 5–15 atoms, from 1–4 of which are heteroatoms selected from O, S(O)$_y$ wherein y is 0, 1 or 2, and N. Examples of heteroaryl groups include: pyridyl, furyl, thienyl, thiazolyl, isothiazolyl, imidazolyl, benzimidazolyl, pyrazinyl, pyrimidyl, quinolyl, isoquinolyl, benzofuryl, benzothienyl, pyrazolyl, indolyl, purinyl, isoxazolyl, oxazolyl, thiadiazolyl, furazan and similar groups.

Heterocyclyl and heterocycle refer to mono- bi- and tricyclic groups having from 5–15 atoms, and 1–4 heteroatoms, selected from O, S(O)$_y$ wherein y is 0, 1 or 2, and N. The group does not have alternating or resonating double bonds throughout. Examples of heterocyclic groups include piperidine, piperazine, pyrrolidine, morpholine, tetrahydrofuran, tetrahydrothiophene, tetrahydropyran and similar groups.

Preferred values of Z include H, halo, $C_{1-7}$ alkyl and halo $C_{1-7}$ alkoxy, and Z combined with 1 $R^1$ group to represent a fused aryl, heteroaryl or heterocyclyl group, optionally substituted with 1–4 halo groups. Within this subset all other variables are as originally defined.

Preferably 0–3 $R^1$ are present and when present, are independently selected from: halo, $C_{1-7}$ alkyl, O$C_{1-7}$ alkyl, and halo$C_{1-7}$ alkoxy. Within this subset all other variables are as originally defined.

Preferably $R^3$ represents H or $C_{1-7}$ alkyl, and more preferably $R^3$ represents H. Within this subset all other variables are as originally defined.

Preferably $R^4$ represents H or $C_{1-7}$ alkyl, and more preferably $R^4$ represents H. Within this subset all other variables are as originally defined.

Preferably $C_{1-7}$ alkyl as shown in formula I represents $C_{1-4}$ alkyl, and more preferably methylene. Within this subset all other variables are as originally defined.

Preferred $R^2$ groups are H and aryl, said aryl being optionally substituted with 1–3 groups selected from: halo, OH, $C_{1-7}$ alkyl, O$C_{1-7}$ alkyl, halo$C_{1-7}$ alkyl and halo$C_{1-7}$ alkoxy.

Preferably the compound of formula I is in the form of a pharmaceutically acceptable salt, most preferably the chloride salt.

A preferred subset of compounds can be described in connection with formula I including the pharmaceutically acceptable salts and hydrates thereof, wherein:

Z is selected from the group consisting of: H, halo, $C_{1-7}$ alkyl and halo $C_{1-7}$ alkoxy, or Z is combined with 1 $R^1$ group to represent a fused aryl, heteroaryl or heterocyclyl group, optionally substituted with 1–4 halo groups;

0–3 $R^1$ are present and when present, are independently selected from: halo, $C_{1-7}$ alkyl, O$C_{1-7}$ alkyl, and halo$C_{1-7}$ alkoxy;

$R^3$ represents H or $C_{1-7}$ alkyl;

$R^4$ represents H or $C_{1-7}$ alkyl;

$C_{0-6}$ alkyl represents $C_{1-4}$ alkyl, and $R^2$ represents H or aryl, said aryl being optionally substituted with 1–3 groups selected from: halo, OH, $C_{1-7}$ alkyl, $OC_{1-7}$ alkyl, and $haloC_{1-7}$ alkoxy.

A subset of compounds that is of particular interest is represented by formula II:

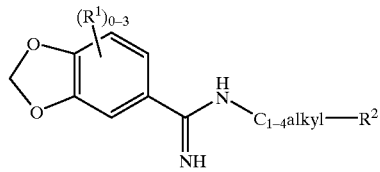

II wherein the —CH$_2$— of the methylenedioxy group is optionally substituted with 1–2 halo or $C_{1-7}$ alkyl groups, and $R^1$ and $R^2$ are as originally defined.

Another subset of compounds that is of particular interest is represented by formula III:

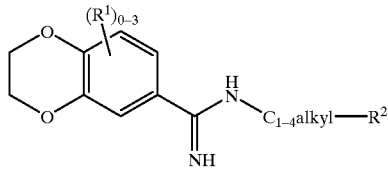

III wherein the —CH$_2$CH$_2$— of the ethylenedioxy group is optionally substituted with 1–4 halo or $C_{1-7}$ alkyl groups, and $R^1$ and $R^2$ are as originally defined.

Another subset of compounds that is of particular interest is represented by formula IV:

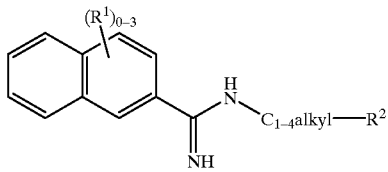

IV wherein the distal phenyl ring of the naphthyl group is optionally substituted with 1–4 halo or $C_{1-7}$ alkyl groups, and $R^1$ and $R^2$ are as originally defined.

Another subset of compounds that is of particular interest is represented by formula V:

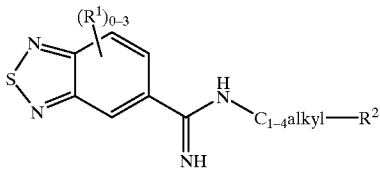

V wherein $R^1$ and $R^2$ are as originally defined.

Another subset of compounds that is of particular interest is represented by formula VI:

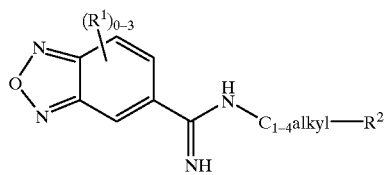

VI wherein $R^1$ and $R^2$ are as originally defined.

Representative compounds of formula I are shown in the examples.

The present invention includes all isomers, tautomers, racemic and resolved, enantiomerically pure forms and salts thereof.

Some of the compounds described herein contain olefinic double bonds. The invention includes all E and Z geometric isomers.

The term "pharmaceutically acceptable salts" refers to salts prepared from pharmaceutically acceptable bases including inorganic bases and organic bases. Representative salts derived from inorganic bases include aluminum, ammonium, calcium, copper, ferric, ferrous, lithium, magnesium, manganic salts, manganous, ammonium, potassium, sodium, zinc and the like. Particularly preferred are the calcium, magnesium, potassium, and sodium salts. Representative salts derived from pharmaceutically acceptable organic bases include salts of primary, secondary and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Examples of such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like.

In the discussion of method of treatment which follows, reference to the compound of formula I includes pharmaceutically acceptable salts, hydrates, enantiomers, tautomers and the like, as well as salts of such enantiomers.

The compound of Formula I is useful for the relief of neurological and neurodegenerative diseases, including pain, (and in particular neuropathic pain), epilepsy, stroke, anxiety, cerebral ischemia, muscular spasms, Alzheimer's Disease, Huntington's Disease and Parkinson's Disease.

For the treatment of any of these neurological and neurodegenerative diseases, a compound of formula I is administered in an amount that is effective to treat or prevent said disease or condition. The compound may be administered orally, topically, parenterally, by inhalation spray or rectally in dosages containing conventional non-toxic pharmaceutically acceptable diluents, adjuvants and vehicles. The term parenteral as used herein includes subcutaneous, intravenous, intramuscular, intradermal, epidural, and intrasternal injection or infusion techniques. In addition to the treatment of warm-blooded animals such as mice, rats, horses, cattle sheep, dogs, cats, etc., the compounds of the invention are effective for the treatment or prevention of neurological and neurodegenerative diseases in humans.

The therapeutic dose of the compound of formula I will, of course, vary with the nature or severity of the condition to be treated, the particular compound selected, its route of administration and other factors. It will also vary according to the age, weight and response of the individual patient. An effective dosage amount of the compound can thus be determined by the clinician after consideration of all these criteria, using his or her best judgement on the patient's behalf. A representative dose ranges from about 0.001 mpk/day to about 100 mpk/day.

The pharmaceutical composition of the present invention comprises a compound of formula I or a salt or hydrate thereof in combination with a pharmaceutically acceptable carrier. Optionally other therapeutic ingredients may be included as well. Examples of dosage forms include tablets, troches, dispersions, suspensions, solutions, capsules, creams, ointments, aerosols and the like.

The compositions may be presented in multiple dosage containers or in unit dosage form and prepared by methods well-known in the art of pharmacy.

The compounds of formula I can be combined as the active ingredient with the pharmaceutical carrier according to conventional pharmaceutical compounding techniques. The carrier may take a wide variety of forms depending on the form desired. In preparing oral dosage forms, any of the usual pharmaceutical media may be employed, such as, for example, water, alcohols, oils, flavoring agents, preservatives, coloring agents and the like in the case of oral liquid preparations, such as, for example, suspensions, elixirs and solutions; or starches, sugars, microcrystalline cellulose, diluents, granulating agents, lubricants, binders, disintegrating agents and the like in the case of oral solid preparations such as, for example, powders, capsules and tablets. Solid oral preparations are preferred over liquid preparations. If desired, tablets may be coated by standard aqueous or nonaqueous techniques.

Examples of suitable dosage units typically range from about 0.01 mg to about 1.0 g of the active ingredient.

The diseases or conditions described herein may be effectively treated by the administration of from about 0.01 to about 50 mg of the compound per kilogram of body weight per day, or alternatively about 0.5 mg to about 3.5 g per patient per day.

The active ingredient may be combined with the carrier materials to produce the dosage form. For example, a formulation intended for oral administration to humans may contain from about 0.5 mg to about 5 g of the compound, compounded with an appropriate and convenient amount of carrier material which may vary from about 5 to about 95 percent of the total composition. Dosage units will generally contain between from about 1 mg to about 1000 mg of an active ingredient, typically 25 mg, 50 mg, 100 mg, 200 mg, 300 mg, 400 mg, 500 mg, 600 mg, 800 mg, or 1000 mg.

It is understood that the specific dose level for any particular patient depends upon a variety of factors including the age, body weight, general health, sex, diet, time of administration, route of administration, rate of excretion, drug combination and the severity of the particular disease or condition undergoing therapy.

Compounds of the invention can be synthesized in accordance with the following general reaction schemes.

SCHEME 1

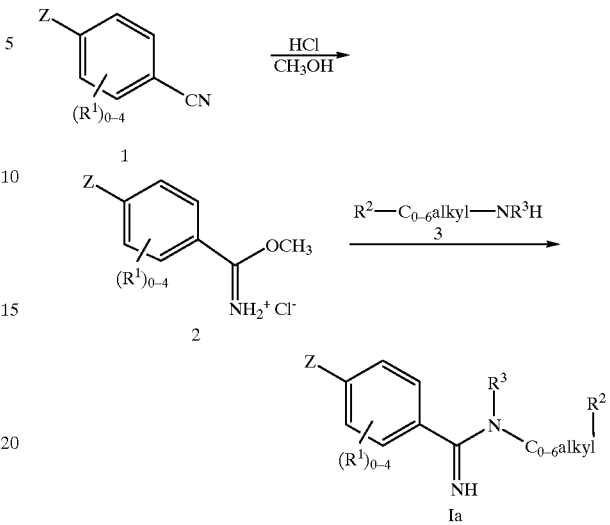

In accordance with scheme 1, hydrogen chloride is bubbled through a solution of the appropriately substituted benzonitrile 1 in methanol at room temperature. The volatiles are removed under reduced pressure and the resulting residue is triturated with ether and filtered to yield the desired imidate 2. Imidate 2 is dissolved in methanol at ambient temperature, treated with amine 3 at ambient temperature and stirred under argon. The volatiles are removed under reduced pressure and the residue purified by preparative HPLC or trituration with ether to afford amidine Ia.

SCHEME 2

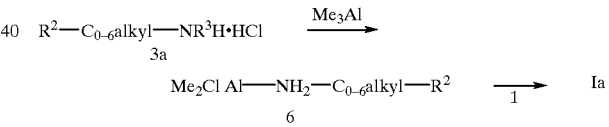

In accordance with scheme 2, at room temperature under argon, amine 3a is dissolved in ether and was treated with 1-M hydrogen chloride in ether (1 equiv.) in a single portion. The resulting precipitate is stirred vigorously for 10 minutes. The volatiles are removed under reduced pressure. The residue is suspended in toluene, cooled to 0° C. under argon, treated with 2.0-M trimethylaluminum (1.05 equiv.) in a dropwise manner, and stirred for 45 minutes at room temperature to afford intermediate 6 (not isolated). Compound 6 is added to a solution of nitrile 1 in toluene. The reaction is heated to 80° C. without stirring in a sealed tube for 18 h, cooled to ambient temperature, poured onto a silica gel column and eluted with methanol/dichloromethane to give the amidine 4.

EXAMPLES

Using the procedures described in the general synthesis schemes above, starting with readily available starting materials, or making routine modifications thereto, the following compounds were prepared.

| Ex. No. | Structure/Name | Mass Spec. |
|---|---|---|
| 1 | 2,2,3,3-Tetrafluoro-N-indan-1-yl-2,3-dihydro-benzo[1,4]dioxine-6-carboxamidine | M/Z (ES+) 367 ([M + H]+) |
| 2 | N-Cyclopropylmethyl-2,2,3,3-tetrafluoro-2,3-dihydro-benzo[1,4]dioxine-6-carboxamidine | M/Z (ES+) 305 ([M + H]+) |
| 3 | N-Butyl-2,2,3,3-tetrafluoro-2,3-dihydro-benzo[1,4]dioxine-6-carboxamidine | M/Z (ES+) 307 ([M + H]+) |
| 4 | N-(3,5-Dimethyl-benzyl)-2,2,3,3-tetrafluoro-2,3,4a,8a-tetrahydro-benzo[1,4]dioxine-6-carboxamidine | M/Z (ES+) 369 ([M + H]+) |
| 5 | 2,2,3,3-Tetrafluoro-N-(3-trifluoromethoxy-benzyl)-2,3,4a,8a-tetrahydro-benzo[1,4]dioxine-6-carboxamidine | M/Z (ES+) 425 ([M + H]+) |

-continued

| Ex. No. | Structure/Name | Mass Spec. |
|---|---|---|
| 6 | N-(3,5-Dichloro-benzyl)-2,2,3,3-tetrafluoro-2,3,4a,8a-tetrahydro-benzo[1,4]dioxine-6-carboxamidine | M/Z (ES$^+$) 409 ([M + H]$^+$) |
| 7 | 2,2,3,3-Tetrafluoro-N-(2-methoxy-benzyl)-2,3,4a,8a-tetrahydro-benzo[1,4]dioxine-6-carboxamidine | M/Z (ES$^+$) 371 ([M + H]$^+$) |
| 8 | 2,2,3,3-Tetrafluoro-N-(2-trifluoromethyl-benzyl)-2,3,4a,8a-tetrahydro-benzo[1,4]dioxine-6-carboxamidine | M/Z (ES$^+$) 409 ([M + H]$^+$) |
| 9 | 2,2,3,3-Tetrafluoro-N-(3-methoxy-benzyl)-2,3,4a,8a-tetrahydro-benzo[1,4]dioxine-6-carboxamidine | M/Z (ES$^+$) 371 ([M + H]$^+$) |
| 10 | N-(3-Chloro-benzyl)-4-trifluoromethoxy-benzamidine | M/Z (ES$^+$) 329/331 ([M + H]$^+$) |

-continued

| Ex. No. | Structure/Name | Mass Spec. |
|---|---|---|
| 11 | 4-Trifluoromethoxy-N-(2-trifluoromethoxy-benzyl)-benzamidine | M/Z (ES+) 379 ([M + H]+) |
| 12 | 4-Trifluoromethoxy-N-(3-trifluoromethoxy-benzyl)-benzamidine | M/Z (ES+) 379 ([M + H]+) |
| 13 | N-(2-Methoxy-benzyl)-4-trifluoromethoxy-benzamidine | M/Z (ES+) 325 ([M + H]+) |
| 14 | N-(3-Methoxy-benzyl)-4-trifluoromethoxy-benzamidine | M/Z (ES+) 325 ([M + H]+) |
| 15 | N-(3,5-Dichloro-benzyl)-4-trifluoromethoxy-benzamidine | M/Z (ES+) 363 ([M + H]+) |
| 16 | N-(3,5-Dichloro-benzyl)-4-trifluoromethoxy-benzamidine | M/Z (ES+) 323 ([M + H]+) |

-continued

| Ex. No. | Structure/Name | Mass Spec. |
|---|---|---|
| 17 | 4-Trifluoromethoxy-N-(2-trifluoromethyl-benzyl)-benzamidine | M/Z (ES+) 363 ([M + H]+) |
| 18 | 4-Trifluoromethoxy-N-(2-trifluoromethyl-benzyl)-benzamidine | M/Z (ES+) 495 ([M + H]+) |
| 19 | N-Phenethyl-4-trifluoromethoxy-benzamidine | M/Z (ES+) 309 ([M + H]+) |
| 20 | 3,4-Dichloro-N-(2-trifluoromethoxy-benzyl)-benzamidine | M/Z (ES+) 363 ([M + H]+) |
| 21 | 3,4-Dichloro-N-(3-trifluoromethoxy-benzyl)-benzamidine | M/Z (ES+) 363 ([M + H]+) |
| 22 | 3,4-Dichloro-N-(2-methoxy-benzyl)-benzamidine | M/Z (ES+) 309 ([M + H]+) |

-continued

| Ex. No. | Structure/Name | Mass Spec. |
|---|---|---|
| 23 | 3,4-Dichloro-N-(2-methoxy-benzyl)-benzamidine | M/Z (ES+) 309 ([M + H]+) |
| 24 | 3,4-Dichloro-N-(3,5-dichloro-benzyl)-benzamidine | M/Z (ES+) 347 ([M + H]+) |
| 25 | 3,4-Dichloro-N-(3,5-dimethyl-benzyl)-benzamidine | M/Z (ES+) 307 ([M + H]+) |
| 26 | 3,4-Dichloro-N-(2-trifluoromethyl-benzyl)-benzamidine | M/Z (ES+) 347 ([M + H]+) |
| 27 | 3,4-Dichloro-N-(3-chloro-benzyl)-benzamidine | M/Z (ES+) 313 ([M + H]+) |
| 28 | 3,4-Dichloro-N-phenethyl-benzamidine | M/Z (ES+) 293 ([M + H]+) |

| Ex. No. | Structure/Name | Mass Spec. |
|---|---|---|
| 29 | N-(2-Trifluoromethoxy-benzyl)-benzo[1,2,5]thiadiazole-5-carboxamidine | M/Z (ES$^+$) 353 ([M + H]$^+$) |
| 30 | N-(3-Trifluoromethoxy-benzyl)-benzo[1,2,5]thiadiazole-5-carboxamidine | M/Z (ES$^+$) 353 ([M + H]$^+$) |
| 31 | N-(2-Methoxy-benzyl)-benzo[1,2,5]thiadiazole-5-carboxamidine | M/Z (ES$^+$) 299 ([M + H]$^+$) |
| 32 | N(3-Methoxy-benzyl)-benzo[1,2,5]thiadiazole-5-carboxamidine | M/Z (ES$^+$) 299 ([M +H]$^+$) |
| 33 | N-(3,5-Dichloro-benzyl)-benzo[1,2,5]thiadiazole-5-carboxamidine | M/Z (ES$^+$) 337 ([M + H]$^+$) |
| 34 | N-(3,5-Dimethyl-benzyl)-benzo[1,2,5]thiadiazole-5-carboxamidine | M/Z (ES$^+$) 297 ([M + H]$^+$) |

-continued

| Ex. No. | Structure/Name | Mass Spec. |
|---|---|---|
| 35 | 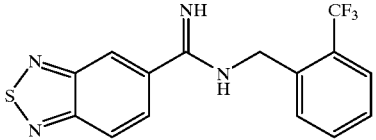<br>N-(2-Trifluoromethyl-benzyl)-benzo[1,2,5]thiadiazole-5-carboxamidine | M/Z (ES+) 337 ([M + H]+) |
| 36 | 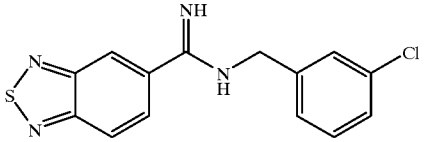<br>N-(3-Chloro-benzyl)-benzo[1,2,5]thiadiazole-5-carboxamidine | M/Z (ES+) 303/305 ([M + H]+) |
| 37 | 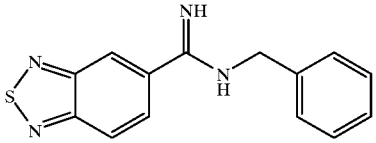<br>N-Benzyl-benzo[1,2,5]thiadiazole-5-carboxamidine | M/Z (ES+) 269 ([M + H]+) |
| 38 | 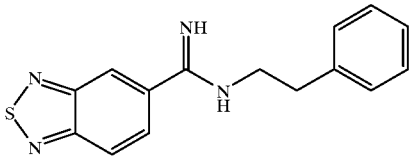<br>N-Benzyl-benzo[1,2,5]thiadiazole-5-carboxamidine | M/Z (ES+) 283 ([M + H]+) |
| 39 | <br>N-(3-Chloro-benzyl)-2,2-difluoro-benzo[1,3]dioxole-5-carboxamidine | M/Z (ES+) 325 ([M + H]+) |
| 40 | 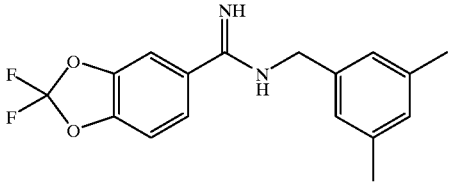<br>N-(3,5-Dimethyl-benzyl)-2,2-difluoro-benzo[1,3]dioxole-5-carboxamidine | M/Z (ES+) 319 ([M + H]+) |

-continued

| Ex. No. | Structure/Name | Mass Spec. |
|---|---|---|
| 41 | 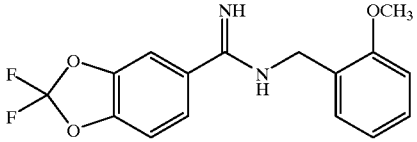<br>2,2-Difluoro-N-(2-methoxy-benzyl)-benzo[1,3]dioxole-5-carboxamidine | M/Z (ES$^+$) 291 ([M + H]$^+$) |
| 42 | 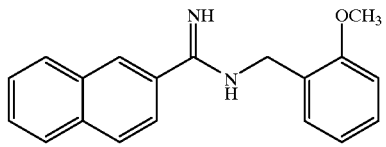<br>N-(2-Methoxy-benzyl)-naphthalene-2-carboxamidine | M/Z (ES$^+$) 291 ([M + H]$^+$) |
| 43 | 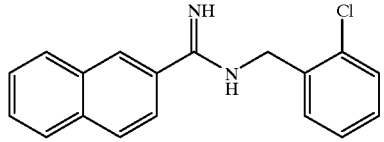<br>N-(2-Chloro-benzyl)-naphthalene-2-carboxamidine | M/Z (ES$^+$) 295/297 ([M + H]$^+$) |
| 44 | 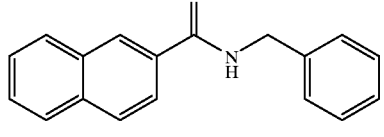<br>N-Benzyl-naphthalene-2-carboxamidine | M/Z (ES$^+$) 261 ([M + H]$^+$) |
| 45 | 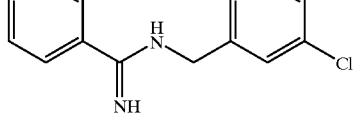 | M/Z (ES$^+$) 245 ([M + H]$^+$) |
| 46 | 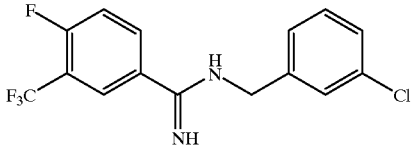 | M/Z (ES$^+$) 331 ([M + H]$^+$) |
| 47 | 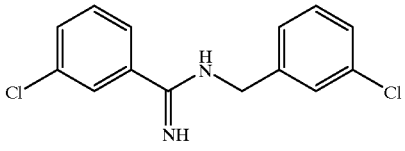 | M/Z (ES$^+$) 279 ([M + H]$^+$) |

-continued

| Ex. No. | Structure/Name | Mass Spec. |
|---|---|---|
| 48 | 4-Cl-C6H4-C(=NH)-NH-CH2-C6H4-3-Cl | M/Z (ES+) 279 ([M + H]+) |
| 49 | 3-F-C6H4-C(=NH)-NH-CH2-C6H4-3-Cl | M/Z (ES+) 263 ([M + H]+) |
| 50 | 4-F-C6H4-C(=NH)-NH-CH2-C6H4-3-Cl | M/Z (ES+) 263 ([M + H]+) |
| 51 | 3-F3C-C6H4-C(=NH)-NH-CH2-C6H4-3-Cl | M/Z (ES+) 313 ([M + H]+) |
| 52 | 3-F3CO-C6H4-C(=NH)-NH-CH2-C6H4-3-Cl | M/Z (ES+) 329 ([M + H]+) |
| 53 | 4-Br-C6H4-C(=NH)-NH-CH2-C6H4-3-Cl | M/Z (ES+) 323 ([M + H]+) |
| 54 | 4-CH3-3-Cl-C6H3-C(=NH)-NH-CH2-C6H4-3-Cl | M/Z (ES+) 293 ([M + H]+) |
| 55 | 3,4-di-F-C6H3-C(=NH)-NH-CH2-C6H4-3-Cl | M/Z (ES+) 281 ([M + H]+) |
| 56 | 4-F-3-Br-C6H3-C(=NH)-NH-CH2-C6H4-3-Cl | M/Z (ES+) 341 ([M + H]+) |

-continued
| Ex. No. | Structure/Name | Mass Spec. |
|---|---|---|
| 57 | 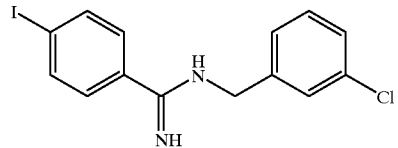 | M/Z (ES+) 371 ([M + H]+) |
| 58 | 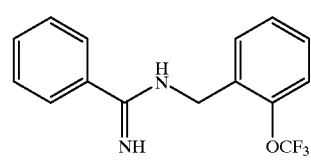 | M/Z (ES+) 295 ([M + H]+) |
| 59 | 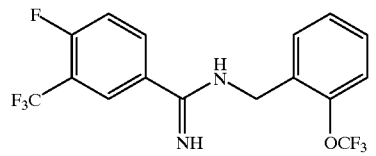 | M/Z (ES+) 381 ([M + H]+) |
| 60 | 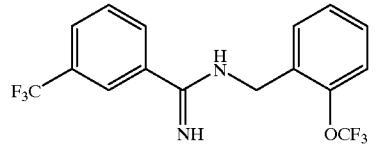 | M/Z (ES+) 363 ([M + H]+) |
| 61 | 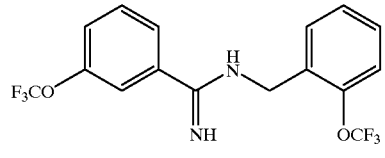 | M/Z (ES+) 379 ([M + H]+) |
| 62 | 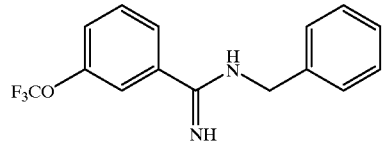 | M/Z (ES+) 295 ([M + H]+) |
| 63 | 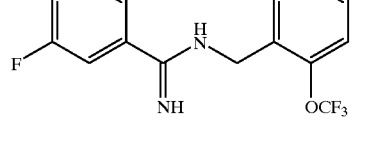 | M/Z (ES+) 331 ([M + H]+) |
| 64 | 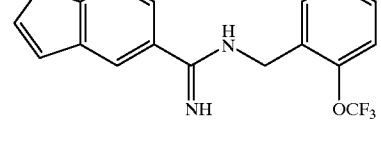 | M/Z (ES+) 334 ([M + H]+) |
| 65 | 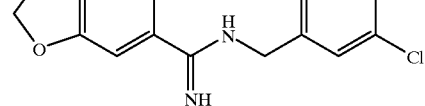 | M/Z (ES+) 289 ([M + H]+) |

-continued
| Ex. No. | Structure/Name | Mass Spec. |
|---|---|---|
| 66 | 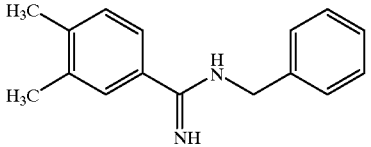 | M/Z (ES+) 239 ([M + H]+) |
| 67 | 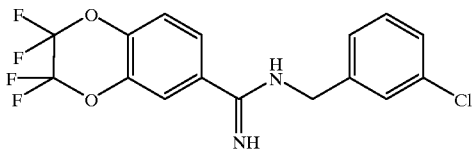 | M/Z (ES+) 375 ([M + H]+) |
| 68 | 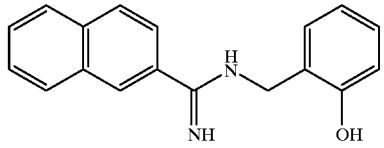 | M/Z (ES+) 277 ([M + H]+) |
| 69 | 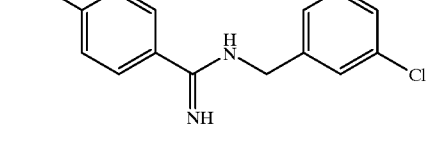 | MIZ (ES+) 275 ([M + H]+) |
| 70 | 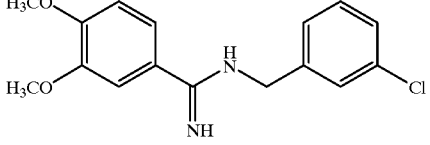 | MIZ (ES+) 305 ([M + H]+) |
| 71 | 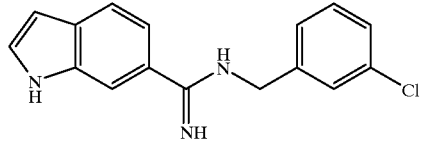 | M/Z (ES+) 284 ([M + H]+) |
| 72 | 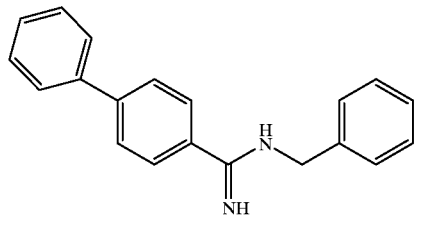 | M/Z (ES+) 287 ([M + H]+) |
| 73 | 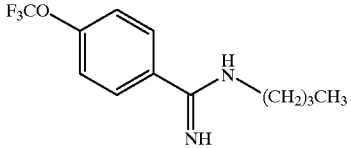 | M/Z (ES+) 261 ([M + H]+) |
| 74 | 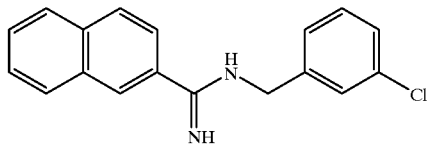 | M/Z (ES+) 295 ([M + H]+) |

| Ex. No. Structure/Name | Mass Spec. |
|---|---|
| 75 | M/Z (ES+) 354 ([M + H]+) |
| 76 | M/Z (ES+) 425 ([M + H]+) |
| 77 | M/Z (ES+) 416 ([M + H]+) |
| 78 | M/Z (ES+) 367 ([M + H]+) |
| 79 | M/Z (ES+) 339 ([M + H]+) |
| 80 | M/Z (ES+) 309 ([M + H]+) |
| 81 | M/Z (ES+) 261 ([M + H]+) |
| 82 | M/Z (ES+) 339 ([M + H]+) |

-continued

| Ex. No. | Structure/Name | Mass Spec. |
|---|---|---|
| 83 | 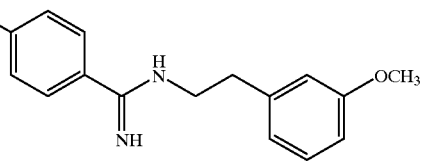 | M/Z (ES+) 325 ([M + H]+) |

Biological Assay

The following assays are used to demonstrate biological activity and utility for the compounds of formula I.

[$^3$H] Ifenprodil binding to recombinant human NR1a/NR2B receptors

Ifenprodil is an NMDA receptor antagonist which acts through a distinct modulatory site to those of glutamate, glycine and MK-801 and is selective for NR2B-containing receptors (Grimwood et al., 1996a). [$^3$H] Ifenprodil binding to cell membranes expressing recombinant human NR1a/NR2B receptors was essentially as described by Grimwood et al. (1996b). In brief, 100 μg of cell homogenate was incubated with [$^3$H] Ifenprodil (NEN) and 50 mM Tris acetate buffer (pH 7.0) on ice. Non-specific binding is determined by addition of 10 micromolar CP-101,606 to a series of wells. After 2 hours, free radioactivity was separated from bound by filtration through Whatman GF/B filters using a cell harvester. Filters were soaked overnight in scintillation fluid and levels of radioactivity determined using a scintillation counter. Inhibition curves were analysed assuming a one-site model.

Generally the compounds described herein demonstrate a 50% inhibition of Ifenprodil binding at a concentration of less than 5 μM.

Functional Ca++ Antagonism Assay-FLIPR

Human NR1a/2B receptor transfected cells are plated in a 96-well format and grown for one day in normal growth media (Dulbeccos MEM with Na pyruvate). NR1a/2B-expression in these cells is induced by the addition of dexamethasone in the presence of ketamine for 16–24 hours. After receptor induction cells are washed with assay buffer (Hanks balanced salt solution (HBSS-Mg free) containing 20 mM HEPES, 0.1% BSA, 2 mM CaCl$_2$ and 250 uM probenecid). Each 96 well cell plate is loaded with the Ca++ sensitive dye Fluo-3 (Molecular Probes, Inc.) in assay buffer. The cells are then washed with assay buffer leaving them in 100 ul buffer. Test compounds in solution are pipetted by FLIPR (Fluorometric Imaging Plate Reader, Molecular Dynamics) for 2 min pretreatment. During this time the fluorescence intensity is recorded (excitation at 488 nm and emission at 530 nm). The glutamate/glycine 50 ul agonist solution (final concentration 1 uM/1 uM) is then added by FLIPR into each well already containing 150 ul of buffer (containing the test compound or vehicle) and the fluorescence is continuously monitored for 10 min. Fluorescence values in the presence of an antagonist are compared to those for the agonist alone.

Carrageenan-induced mechanical hyperalgesia in rats

The ability of the agents to reverse carrageenan induced hyperalgesia is determined using the method described by Boyce et al. (1994). Essentially, the animal's hind paw is positioned over a convex surface and gradually increasing pressure applied to the dorsal surface until the animals vocalizes or withdraws. The mechanical thresholds are determined for both hind paws to provide a baseline for comparison following injection of carrageenan into one paw. Rats receive an intraplantar injection of carrageenan or saline into one hind paw and mechanical thresholds of both hind paws are re-determined 3 h later. Carrageenan-induced hyperalgesia is defined as the difference in threshold between rats that receive intraplantar injection of saline or carrageenan. Test compounds are administered 2 hours after carrageenan and hyperalgesia expressed as a percentage inhibition induced by carrageenan.

All citations contained herein are hereby incorporated by reference in their entirety.

Boyce, S., Chan, C.-C., Gordon, R., Li, C.-S., Rodger, I. W., Webb, J. K., Rupniak, N. M. J., Hill, R. G., 1994. L-745,337: a selective inhibitor of cyclooxygenase-2 elicits antinociception but not gastric ulceration in rats. Neuropharmacology 33, 1609–1611.

Boyce, S., Wyatt, A., Webb, J. K., O'Donnell, R., Mason, G., Rigby, M., Sirinathsinghji, D., Hill, R. G., & Rupniak, N. M. J. 1999. Selective NMDA NR2B antagonists induce antinociception without motor dysfunction: correlation with restricted localisation of NR2B subunit in dorsal horn. Neuropharmacology 38: 611–623.

Eide, K., Stubhaug, H., Oye, I., Breivik, H., 1995. Continuous subcutaneous administration of the N-methyl-D-aspartate (NMDA) receptor antagonist ketamine in the treatment of postherpetic neuralgia. Pain 61: 221–228.

Grimwood, S., Gilbert, E., Ragan, C. I., Hutson, P. H., 1996a. Modulation of 45 Ca 2++ influx into cells stably expressing recombinant human NMDA receptors by ligands acting at distinct recognition sites. J. Neurochem. 66, 2589–2595.

Grimwood, S., Le Bourdelles, B., Atack, J. R., Barton, C., Cockett, W., Cook, S. M., Gilbert, E., Hutson, P. H., McKernan, R. M., Myers, J., Ragan, C. I., Wingrove, P. B., & Whiting, P. J. 1996b. Generation and characterisation of stable cell lines expressing recombinant human N-methyl-D-aspartate receptor subtypes. Journal of Neurochemistry 66:2239–2247.

Hornykiewcz, O. 1966. Dopamine and brain function. Pharmacol. Rev. 18:925–964.

Ishii, T., Mornyoshi, K., Sugihara, H., Sakurada, K., Kadotani, H., Yokoi, M., Akazawa, C., Shigemoto, R., Mizuno, N., Masu, M. et al., 1993. Molecular characterization of the family of the N-methyl-D-aspartate receptor subunits. J. Biol. Chem., 268, 2836–2843.

Knox, D. J., McLeod, B. J., Goucke, C. R., 1995. Acute phantom limb pain controlled by ketamine. Anaesth. Intensive Care 23, 620–622.

Kristensen, J. D., Svensson, B., Gordh Jr., T., 1992. The NMDA-receptor antagonist CPP abolishes neurogenic 'wind-up pain' after intrathecal administration in humans. Pain, 51, 249–253.

Laurie, D. J., Bartke, I., Schoepfer, R., Naujoks, K., Seeburg, P. H., 1997. Regional, developmental and interspecies expression of the four NMDAR2 subunits, examined using monoclonal antibodies. Brain Res. Mol. Brain Res. 51,23–32.

Max, M. B., Byas-Smith, M. G., Gracely, R. H., Bennett, G. J., 1995. Intravenous infusion of the NMDA antagonist, ketamine, in chronic posttraumatic pain with allodynia: a double-blind comparison to alfentanil and placebo. Clin. Neuropharmacol. 18, 360–368.

Mitchell, IJ, Hughes, N., Carroll, CB, Brotchie, JM. 1995. Reversal of parkinsonian symptoms by intrastriatal and systemic amnipulations of excitatory amino acid and dopamine transmission in the bilateral 6-OHDA lesioned marmoset. Behav. Pharmacol. 6, 492–507.

Nash, J E, Hill, M P & Brotchie, J M. 1999. Antiparkinsonian Actions of blockade of NR2B-containing NMDA receptors in the Reserpine-treated Rat. Experimental Neurology 155, 42–48.

Sakurada, T., Wako, K., Sugiyama, A., Sakurada, C., Tan-Ko, K., Kisara, K., 1998. Involvement of spinal NMDA receptors in capsaicin-induced nociception. Pharmacol. Biochem. Behav. 59, 339–345.

Taniguchi, K., Shinjo, K., Mizutani, M., Shimada, K., Ishikawa, T., Menniti, F. S., Nagahisa, A., 1997. Antinociceptive activity of CP-101,606, an NMDA receptor NR2B subunit antagonist. Br. J. Pharmacol. 122, 809–812.

Wenzel, A., Scheurer, L., Kunzi, R., Fritschy, J.-M., Mohler, H., Benke, D., 1995. Distribution of NMDA receptor subunit proteins NR2A, 2B, 2C, and 2D in rat brain. NeuroReport 7, 45–48.

Whiting, P J & Priestly, T. 1996. The molecular biology of NMDA type glutamate receptors. In: Turner, A J, Stephenson, FA (eds) Frontiers of Neurobiology 3, Amino Acid Neurotransmission. Portland Press, London, 153–176.

What is claimed is:

1. A compound represented by formula I:

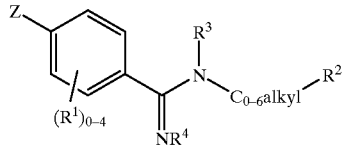

I or a pharmaceutically acceptable salt or hydrate thereof, wherein:

each $R^1$ independently represents a member selected from the group consisting of: halo, $C_{1-7}$ alkyl, haloC$_{1-7}$ alkyl, OH, OC$_{1-7}$ alkyl, and haloC$_{1-7}$ alkoxy, and Z represents a member selected from the group consisting of: H, halo, $C_{1-7}$ alkyl, haloC$_{1-7}$ alkyl, OH, haloC$_{1-7}$ alkoxy and aryl, or one $R^1$ group and Z or two $R^1$ groups taken in combination represent a fused aryl, heteroaryl or heterocyclyl group, said fused group being optionally substituted with 1–4 groups selected from OH, halo, $C_{1-7}$ alkyl, sulfonyl, cyano, OC$_{1-7}$ alkyl, haloC$_{1-7}$ alkyl and haloC$_{1-7}$ alkoxy and the remaining $R^1$ groups are as originally defined;

$R^3$ and $R^4$ independently represent H, $C_{1-7}$ alkyl, $C_{2-4}$ alkenyl, $C_{2-4}$ alkynyl, aryl or heterocyclyl; and $R^2$ represents H, aryl or heteroaryl, said aryl or heteroaryl being optionally substituted with 1–3 groups selected from: halo, OH, $C_{1-7}$ alkyl, OC$_{1-7}$ alkyl, haloC$_{1-7}$ alkyl and haloC$_{1-7}$ alkoxy.

2. A compound in accordance with claim 1 wherein Z is selected from H, halo, $C_{1-7}$ alkyl and halo $C_{1-7}$ alkoxy, or Z is combined with 1 $R^1$ group and represents a fused aryl, heteroaryl or heterocyclyl group, optionally substituted with 1–4 halo groups.

3. A compound in accordance with claim 1 wherein 0–3 $R^1$ groups are present and when present, are independently selected from: halo, $C_{1-7}$ alkyl, OC$_{1-7}$ alkyl, and haloC$_{1-7}$ alkoxy.

4. A compound in accordance with claim 1 wherein $R^3$ represents H or $C_{1-7}$ alkyl.

5. A compound in accordance with claim 4 wherein $R^3$ represents H.

6. A compound in accordance with claim 1 wherein $R^4$ represents H or $C_{1-7}$ alkyl.

7. A compound in accordance with claim 6 wherein $R^4$ represents H.

8. A compound in accordance with claim 1 wherein $C_{0-6}$ alkyl represents $C_{1-4}$ alkyl.

9. A compound om accordance with claim 8 wherein $C_{0-6}$ alkyl represents methylene.

10. A compound in accordance with claim 1 wherein $R^2$ represents H or aryl, optionally substituted with 1–3 groups selected from halo, OH, $C_{1-7}$ alkyl, OC$_{1-7}$ alkyl, haloC$_{1-7}$ alkyl and haloC$_{1-7}$ alkoxy.

11. A compound in accordance with claim 1 in the form of a pharmaceutically acceptable salt.

12. A compound in accordance with claim 1 wherein:

Z is selected from the group consisting of: H, halo, $C_{1-7}$ alkyl and halo $C_{1-7}$ alkoxy, or Z is combined with 1 $R^1$ group to represent a fused aryl, heteroaryl or heterocyclyl group, optionally substituted with 1–4 halo groups;

0–3 $R^1$ are present and when present, are independently selected from: halo, $C_{1-7}$ alkyl, OC$_{1-7}$ alkyl, and haloC$_{1-7}$ alkoxy;

$R^3$ represents H or $C_{1-7}$ alkyl;

$R^4$ represents H or $C_{1-7}$ alkyl;

$C_{0-6}$ alkyl represents $C_{1-4}$ alkyl, and $R^2$ represents H or aryl, said aryl being optionally substituted with 1–3 groups selected from: halo, OH, $C_{1-7}$ alkyl, OC$_{1-7}$ alkyl, haloC$_{1-7}$ alkyl and haloC$_{1-7}$ alkoxy.

13. A compound represented by formula II:

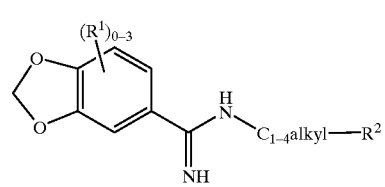

II wherein the —CH$_2$— of the methylenedioxy group is optionally substituted with 1–2 halo or $C_{1-7}$ alkyl groups;

$R^1$ independently represents a member selected from the group consisting of: halo, $C_{1-7}$ alkyl, haloC$_{1-7}$ alkyl, OH, OC$_{1-7}$ alkyl, and haloC$_{1-7}$ alkoxy; and $R^2$ represents H, aryl or heteroaryl, said aryl or heteroaryl being optionally substituted with 1–3 groups selected from: halo, OH, $C_{1-7}$ alkyl, OC$_{1-7}$ alkyl, haloC$_{1-7}$ alkyl and haloC$_{1-7}$ alkoxy.

14. A compound represented by formula III:

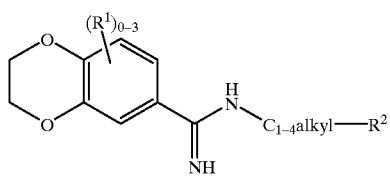

wherein the —CH$_2$CH$_2$— of the ethylenedioxy group is optionally substituted with 1–4 halo or C$_{1-7}$ alkyl groups;

R$^1$ independently represents a member selected from the group consisting of: halo, C$_{1-7}$ alkyl, haloC$_{1-7}$ alkyl, OH, OC$_{1-7}$ alkyl, and haloC$_{1-7}$ alkoxy; and R$^2$ represents H, aryl or heteroaryl, said aryl or heteroaryl being optionally substituted with 1–3 groups selected from: halo, OH, C$_{1-7}$ alkyl, OC$_{1-7}$ alkyl, haloC$_{1-7}$ alkyl and haloC$_{1-7}$ alkoxy.

15. A compound represented by formula IV:

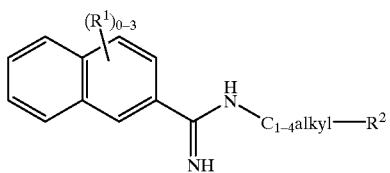

wherein the distal phenyl ring of the naphthyl group is optionally substituted with 1–4 halo or C$_{1-7}$ alkyl groups;

R$^1$ independently represents a member selected from the group consisting of: halo, C$_{1-7}$ alkyl, haloC$_{1-7}$ alkyl, OH, OC$_{1-7}$ alkyl, and haloC$_{1-7}$ alkoxy; and R$^2$ represents H, aryl or heteroaryl, said aryl or heteroaryl being optionally substituted with 1–3 groups selected from: halo, OH, C$_{1-7}$ alkyl, OC$_{1-7}$ alkyl, haloC$_{1-7}$ alkyl and haloC$_{1-7}$ alkoxy.

16. A compound represented by formula V:

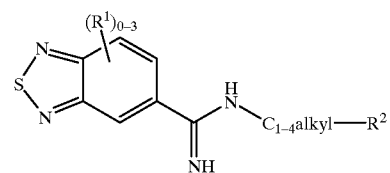

wherein

R$^1$ independently represents a member selected from the group consisting of: halo, C$_{1-7}$ alkyl, haloC$_{1-7}$ alkyl, OH, OC$_{1-7}$ alkyl, and haloC$_{1-7}$ alkoxy; and R$^2$ represents H, aryl or heteroaryl, said aryl or heteroaryl being optionally substituted with 1–3 groups selected from: halo, OH, C$_{1-7}$ alkyl, OC$_{1-7}$ alkyl, haloC$_{1-7}$ alkyl and haloC$_{1-7}$ alkoxy.

17. A compound represented by formula VI:

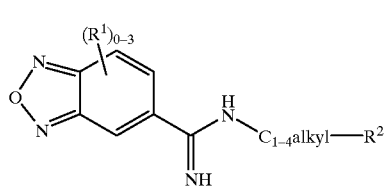

wherein

R$^1$ independently represents a member selected from the group consisting of: halo, C$_{1-7}$ alkyl, haloC$_{1-7}$ alkyl, OH, OC$_{1-7}$ alkyl, and haloC$_{1-7}$ alkoxy; and R$^2$ represents H, aryl or heteroaryl, said aryl or heteroaryl being optionally substituted with 1–3 groups selected from: halo, OH, C$_{1-7}$ alkyl, OC$_{1-7}$ alkyl, haloC$_{1-7}$ alkyl and haloC$_{1-7}$ alkoxy.

18. A compound in accordance with the following table:

| Ex. No. | Structure/Name |
|---|---|
| 1 | 2,2,3,3-Tetrafluoro-N-indan-1-yl-2,3-dihydro-benzo[1,4]dioxine-6-carboxamidine |
| 2 | N-Cyclopropylmethyl-2,2,3,3-tetrafluoro-2,3-dihydro-benzo[1,4]dioxine-6-carboxamidine |
| 3 | N-Butyl-2,2,3,3-tetrafluoro-2,3-dihydro-benzo[1,4]dioxine-6-carboxamidine |
| 4 | N-(3,5-Dimethyl-benzyl)-2,2,3,3-tetrafluoro-2,3,4a,8a-tetrahydro-benzo[1,4]dioxine-6-carboxamidine |

| Ex. No. | Structure/Name |
|---|---|
| 5 | 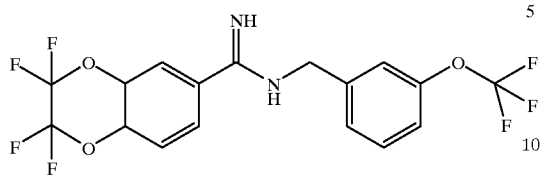
2,2,3,3-Tetrafluoro-N-(3-trifluoromethoxy-benzyl)-2,3,4a,8a-tetrahydro-benzo[1,4]dioxine-6-carboxamidine |
| 6 | 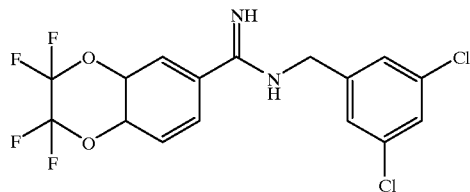
N-(3,5-Dichloro-benzyl)-2,2,3,3-tetrafluoro-2,3,4a,8a-tetrahydro-benzo[1,4]dioxine-6-carboxamidine |
| 7 | 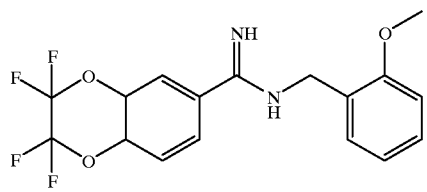
2,2,3,3-Tetrafluoro-N-(2-methoxy-benzyl)-2,3,4a,8a-tetrahydro-benzo[1,4]dioxine-6-carboxamidine |
| 8 | 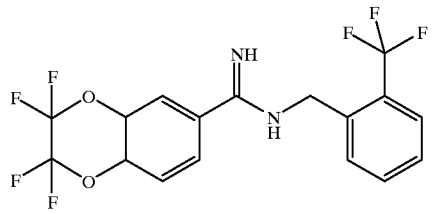
2,2,3,3-Tetrafluoro-N-(2-trifluoromethyl-benzyl)-2,3,4a,8a-tetrahydro-benzo[1,4]dioxine-6-carboxamidine |
| 9 | 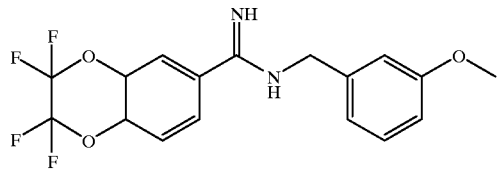
2,2,3,3-Tetrafluoro-N-(3-methoxy-benzyl)-2,3,4a,8a-tetrahydro-benzo[1,4]dioxine-6-carboxamidine |
| 10 | 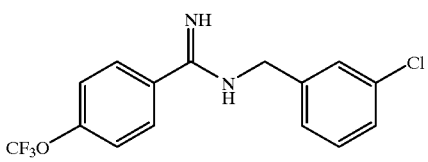
N-(3-Chloro-benzyl)-4-trifluoromethoxy-benzamidine |
| 11 | 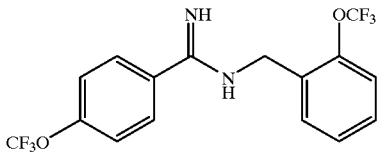
4-Trifluoromethoxy-N-(2-trifluoromethoxy-benzyl)-benzamidine |
| 12 | 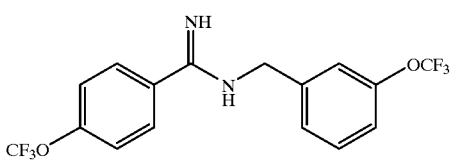
4-Trifluoromethoxy-N-(3-trifluoromethoxy-benzyl)-benzamidine |
| 13 | 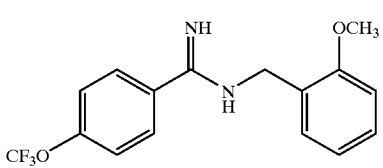
N-(2-Methoxy-benzyl)-4-trifluouomethoxy-benzamidine |
| 14 | 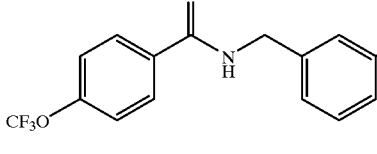
N-(3-Methoxy-benzyl)-4-trifluoromethoxy-benzamidine |
| 15 | 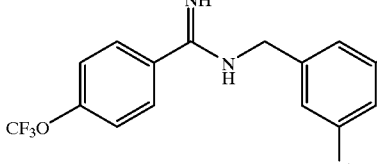
N-(3,5-Dichloro-benzyl)-4-trifluoromethoxy-benzamidine |

| Ex. No. | Structure/Name |
|---|---|
| 16 | 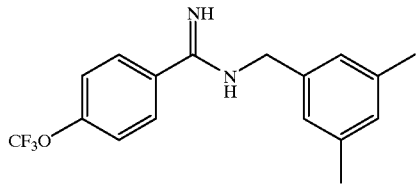<br>N-(3,5-Dichloro-benzyl)-4-trifluoromethoxy-benzamidine |
| 17 | 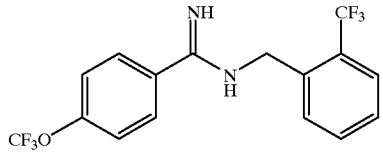<br>4-Trifluoromethoxy-N-(2-trifluoromethyl-benzyl)-benzamidine |
| 18 | 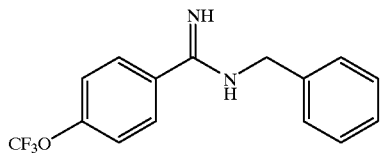<br>4-Trifluoromethoxy-N-(2-trifluoromethyl-benzyl)-benzamidine |
| 19 | 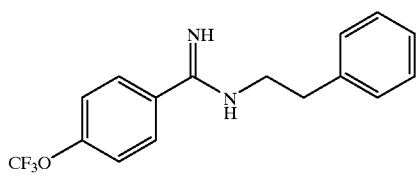<br>N-Phenethyl-4-trifluoromethoxy-benzamidine |
| 20 | 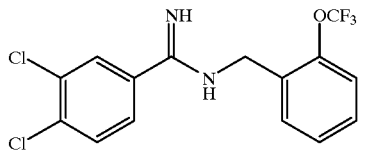<br>3,4-Dichloro-N-(2-trifluoromethoxy-benzyl)-benzamidine |
| 21 | 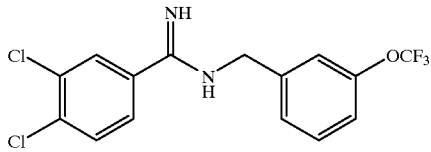<br>3,4-Dichloro-N-(3-trifluoromethoxy-benzyl)-benzamidine |
| 22 | 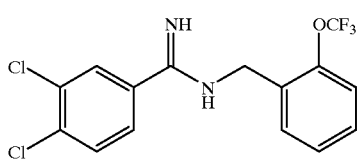<br>3,4-Dichloro-N-(2-methoxy-benzyl)-benzamidine |
| 23 | 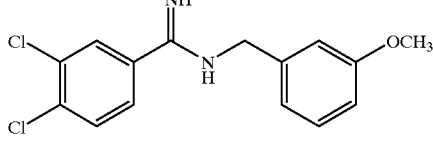<br>3,4-Dichloro-N-(2-methoxy-benzyl)-benzamidine |
| 24 | 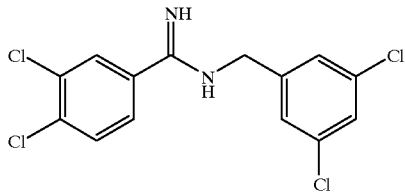<br>3,4-Dichloro-N-(3,5-dichloro-benzyl)-benzamide |
| 25 | 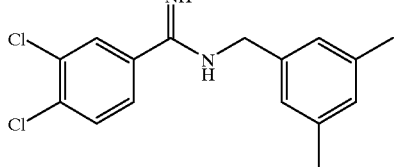<br>3,4-Dichloro-N-(3,5-dimethyl-benzyl)-benzamidine |
| 26 | 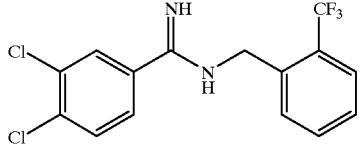<br>3,4-Dichloro-N-(2-trifluoromethyl-benzyl)-benzamidine |
| 27 | 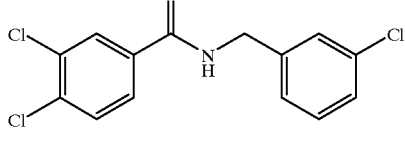<br>3,4-Dichloro-N-(3-chloro-benzyl)-benzamidine |

-continued

| Ex. No. | Structure/Name |
|---|---|
| 28 | 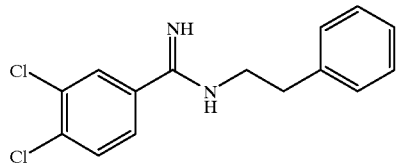

3,4-Dichloro-N-phenethyl-benzamidine |
| 29 | 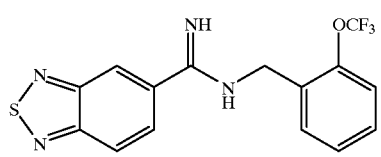

N-(2-Trifluoromethoxy-benzyl)-benzo[1,2,5]thiadiazole-5-carboxamidine |
| 30 | 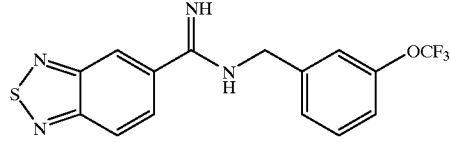

N-(3-Trifluoromethoxy-benzyl)-benzo[1,2,5]thiadiazole-5-carboxamidine |
| 31 | 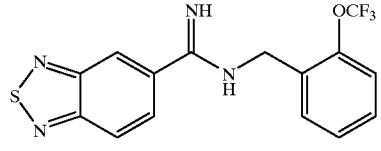

N-(2-Methoxy-benzyl)-benzo[1,2,5]thiadiazole-5-carboxamidine |
| 32 | 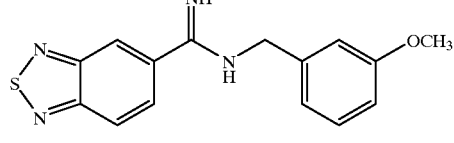

N-(3-Methoxy-benzyl)-benzo[1,2,5]thiadiazole-5-carboxamidine |
| 33 | 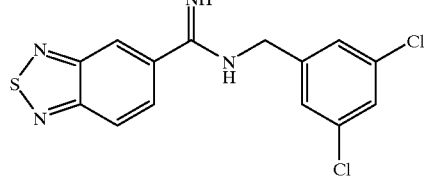

N-(3,5-Dichloro-benzyl)-benzo[1,2,5]thiadiazole-5-carboxamidine |

-continued

| Ex. No. | Structure/Name |
|---|---|
| 34 | 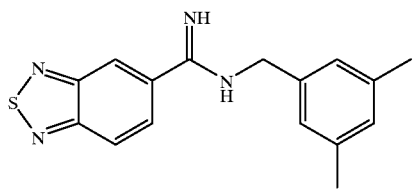

N-(3,5-Dimethyl-benzyl)-benzo[1,2,5]thiadiazole-5-carboxamidine |
| 35 | 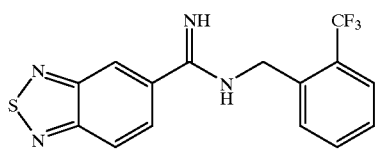

N-(2-Trifluoromethyl-benzyl)-benzo[(1,2,5]thiadiazole-5-carboxamidine |
| 36 | 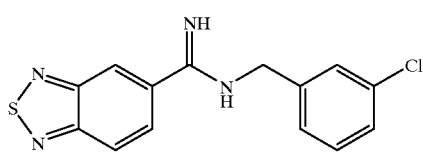

N-(3-Chloro-benzyl)-benzo[1,2,5]thiadiazole-5-carboxamidine |
| 37 | 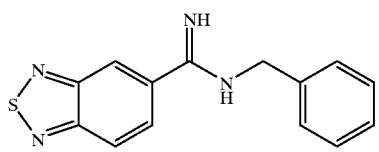

N-Benzyl-benzo[1,2,5]thiadiazole-5-carboxamidine |
| 38 | 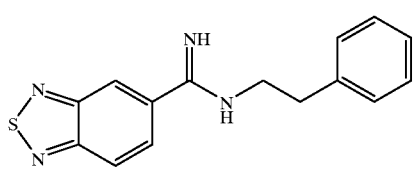

N-Benzyl-benzo[1,2,5]thiadiazole-5-carboxamidine |
| 39 | 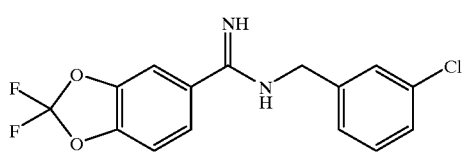

N-(3-Chloro-benzyl)-2,2-difluoro-benzo[1,3]dioxole-5-carboxamidine |

-continued
| Ex. No. | Structure/Name |
|---|---|
| 40 | 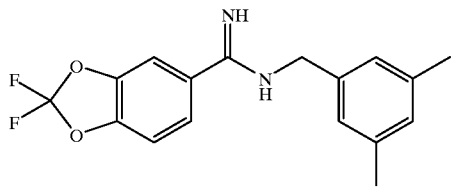<br>N-(3,5-Dimethyl-benzyl)-2,2-difluoro-benzo[1,3]dioxole-5-carboxamidine |
| 41 | 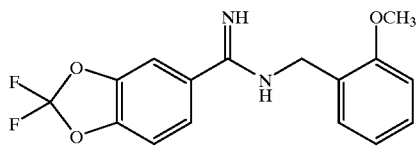<br>2,2-Difluoro-N-(2-methoxy-benzyl)-benzo[1,3]dioxole-5-carboxamidine |
| 42 | 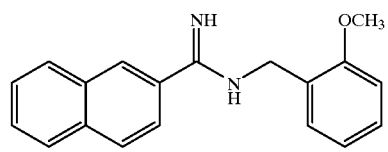<br>N-(2-Methoxy-benzyl)-naphthalene-2-carboxamidine |
| 43 | 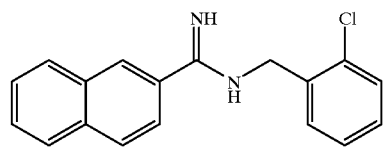<br>N-(2-Chloro-benzyl)-naphthalene-2-carboxamidine |
| 44 | 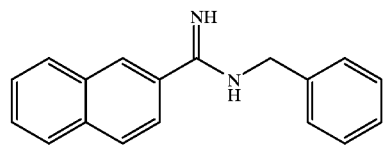<br>N-Benzyl-naphthalene-2-carboxamidine |
| 45 | 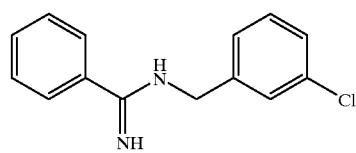 |
| 46 | 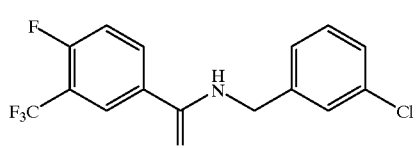 |
-continued
| Ex. No. | Structure/Name |
|---|---|
| 47 | 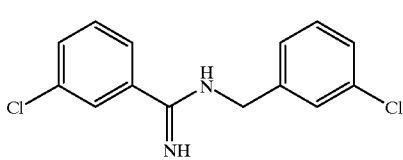 |
| 48 | 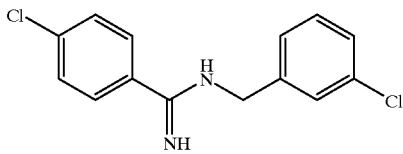 |
| 49 | 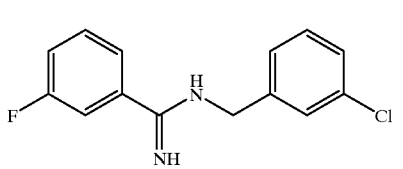 |
| 50 | 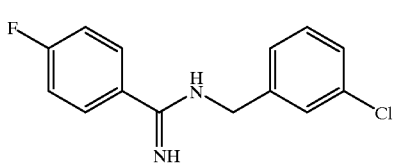 |
| 51 | 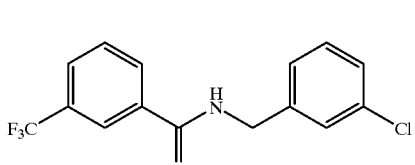 |
| 52 | 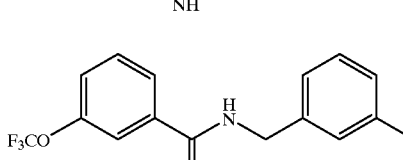 |
| 53 | 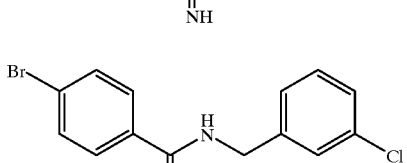 |
| 54 | 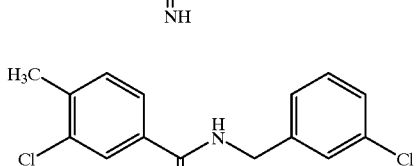 |
| 55 | 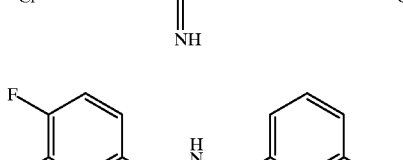 |

-continued

| Ex. No. | Structure/Name |
|---|---|
| 56 | 4-fluoro-3-bromo-N-(3-chlorobenzyl)benzamidine |
| 57 | 4-iodo-N-(3-chlorobenzyl)benzamidine |
| 58 | N-(2-trifluoromethoxybenzyl)benzamidine |
| 59 | 4-fluoro-3-trifluoromethyl-N-(2-trifluoromethoxybenzyl)benzamidine |
| 60 | 3-trifluoromethyl-N-(2-trifluoromethoxybenzyl)benzamidine |
| 61 | 3-trifluoromethoxy-N-(2-trifluoromethoxybenzyl)benzamidine |
| 62 | 3-trifluoromethoxy-N-benzylbenzamidine |
| 63 | 3,4-difluoro-N-(2-trifluoromethoxybenzyl)benzamidine |
| 64 | 1H-indol-5-yl-N-(2-methoxybenzyl)carboxamidine |

-continued

| Ex. No. | Structure/Name |
|---|---|
| 65 | benzo[1,3]dioxol-5-yl-N-(3-chlorobenzyl)carboxamidine |
| 66 | 3,4-dimethyl-N-benzylbenzamidine |
| 67 | 2,2,3,3-tetrafluoro-2,3-dihydro-benzo[1,4]dioxin-6-yl-N-(3-chlorobenzyl)carboxamidine |
| 68 | naphthalen-2-yl-N-(2-hydroxybenzyl)carboxamidine |
| 69 | 4-methoxy-N-(3-chlorobenzyl)benzamidine |
| 70 | 3,4-dimethoxy-N-(3-chlorobenzyl)benzamidine |
| 71 | 1H-indol-6-yl-N-(3-chlorobenzyl)carboxamidine |
| 72 | biphenyl-4-yl-N-benzylcarboxamidine |

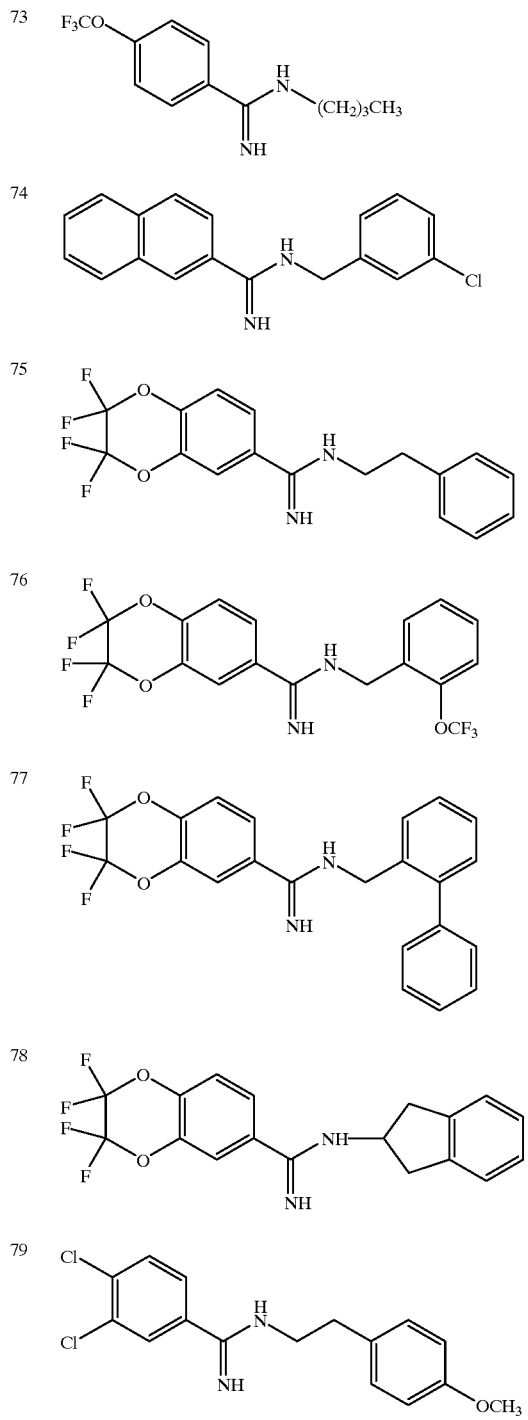
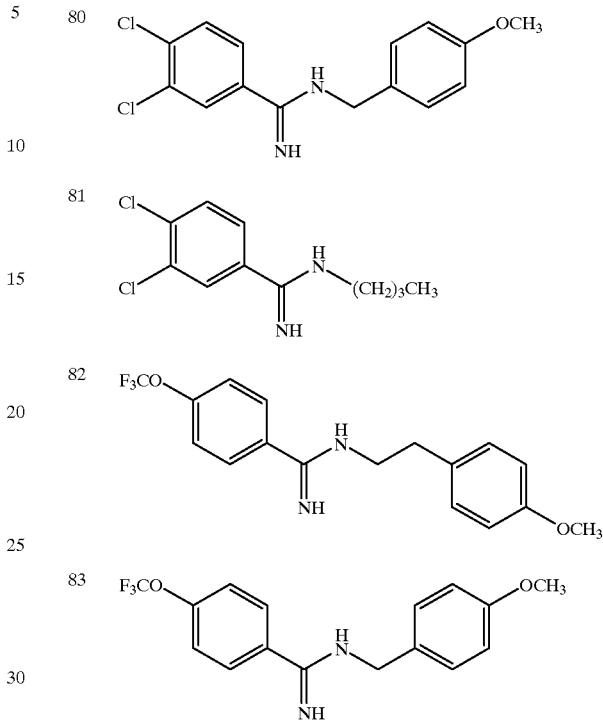

or a pharmaceutically acceptable salt or hydrate thereof.

19. A pharmaceutical composition comprised of a compound in accordance with claim 1 in combination with a pharmaceutically acceptable carrier.

20. A method of treating an NMDA NR2B mediated disease or condition in a mammalian patient in need of such treatment, comprising administering to said patient a compound in accordance with claim 1 in an amount effective to treat said NMDA NR2B mediated disease or condition.

21. A method in accordance with claim 20 wherein the NMDA NR2B mediated disease or condition is selected from the group consisting of: pain, neuropathic pain, epilepsy, stroke, anxiety, cerebral ischemia, muscular spasm, Alzheimer's Disease, Huntington's Disease and Parkinson's Disease.

22. A method in accordance with claim 21 wherein the disease or condition is pain or neuropathic pain.

* * * * *